United States Patent [19]

Kramer

[11] 4,375,557

[45] Mar. 1, 1983

[54] PROCESS FOR THE PREPARATION OF DIHALOVINYLCYCLOPROPANE CARBOXYLIC ACID

[75] Inventor: Petrus A. Kramer, Amsterdam, Netherlands

[73] Assignee: Shell Oil Company, Houston, Tex.

[21] Appl. No.: 385,991

[22] Filed: Jun. 7, 1982

Related U.S. Application Data

[62] Division of Ser. No. 306,106, Sep. 28, 1981, Pat. No. 4,346,038.

[30] Foreign Application Priority Data

Oct. 22, 1980 [GB] United Kingdom ............... 8034067

[51] Int. Cl.³ ............................................. C07C 51/09
[52] U.S. Cl. ..................................... 562/500; 562/506
[58] Field of Search ............................... 562/506, 500

[56] References Cited

U.S. PATENT DOCUMENTS

| | | | |
|---|---|---|---|
| 3,836,568 | 9/1974 | Higo | 562/506 |
| 3,989,654 | 11/1976 | Honda | 562/506 |
| 4,166,063 | 8/1979 | Martel et al. | 260/343.3 |
| 4,237,058 | 12/1980 | Kondo | 562/506 |
| 4,254,282 | 3/1981 | Kondo | 562/506 |
| 4,285,882 | 8/1981 | Kramer | 562/506 |
| 4,289,711 | 9/1981 | Lee | 260/456 |
| 4,294,765 | 10/1981 | Kramer | 260/343.3 |

FOREIGN PATENT DOCUMENTS 2639777 3/1977 Fed. Rep. of Germany.
1561502 2/1980 United Kingdom.

*Primary Examiner*—Michael L. Shippen

[57] ABSTRACT

Novel compounds of the formula I

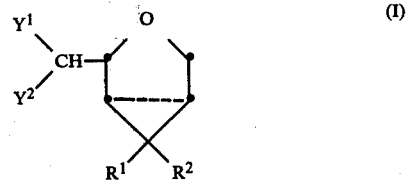

in which each of $Y^1$ and $Y^2$ independently represents a fluorine, chlorine or bromine atom and each of $R^1$ and $R^2$ independently represents a hydrogen atom or an alkyl group having up to 10 carbon atoms, or $R^1$ and $R^2$ together represent an alkylene group having from 2 to 5 carbon atoms, may be converted by the action of base into the corresponding dihalovinylcyclopropane carboxylic acids.

4 Claims, No Drawings

PROCESS FOR THE PREPARATION OF DIHALOVINYLCYCLOPROPANE CARBOXYLIC ACID

This is a division of application Ser. No. 306,106, filed Sept. 28, 1981, now U.S. Pat. No. 4,346,038.

BACKGROUND OF THE INVENTION

1. Field of the Invention

This invention relates to novel oxabicyclo[3.1.0]hexan-2-ones, a process for their preparation and their use in a process for the preparation of dihalovinylcyclopropanecarboxylic acids.

2. Description of the Prior Art

Synthetic pyrethroid insecticides are esters which consist of an acid portion and an alcohol portion. In one group of pyrethroids disclosed in U.S. Pat. No. 4,024,163, the acid portion is derived from a 2,2-dihalovinylcyclopropanecarboxylic acid. Such an acid exists in the form of geometric isomers, in which the 2,2-dihalovinyl and the carboxyl groups are cis or trans to each other. Synthetic pyrethroids in which this acid portion is in the cis form are, in general, more active as insecticides than the corresponding trans compounds, and a great deal of research has been directed towards the preparation of cis 2,2-dihalovinylcyclopropanecarboxylic acids.

The applicant has now found a group of dihalolactones which are convenient to prepare and which can be converted readily into the desired cis dihalovinylcyclopropanecarboxylic acids.

SUMMARY OF THE INVENTION

The present invention is directed to novel compounds of the formula I

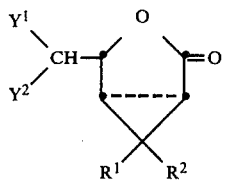

in which each of $Y^1$ and $Y^2$ independently represents a fluorine, chlorine or bromine atom and each of $R^1$ and $R^2$ independently represents a hydrogen atom or an alkyl group having up to 10 carbon atoms, or $R^1$ and $R^2$ together represent an alkylene group having from 2 to 5 carbon atoms.

The substituents $Y^1$ and $Y^2$ may be the same or different, but are preferably the same. Preferably, $Y^1$ and $Y^2$ both represent bromine atoms or, especially, chlorine atoms.

$R^1$ and $R^2$ may be the same or different, but are preferably the same. Preferably each of $R^1$ and $R^2$ represents an alkyl group having 1 to 4, especially 1 or 2, carbon atoms. Most preferably both $R^1$ and $R^2$ represent methyl groups.

Thus an especially preferred compound of the general formula I is the compound in which both of $Y^1$ and $Y^2$ represent chlorine atoms, and both of $R^1$ and $R^2$ represent methyl groups.

Compounds of the general formula I exist in the form of optical and geometric isomers. Thus the compounds may have the R or the S configuration about the cyclopropane carbon atom bearing the —$CO_2$— group, and the $CHY^1Y^2$ group may be endo or exo to the cyclopropane ring. Further possibilities for isomerism exist depending on the meanings of $Y^1$, $Y^2$, $R^1$ and $R^2$. The invention should be understood to include all individual isomers as well as mixtures thereof.

The invention also provides a process for the preparation of a compound of the general formula I, which comprises either reducing a compound of the formula II

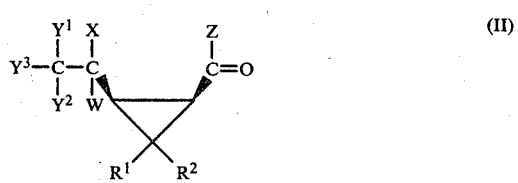

in which $Y^1$, $Y^2$, $R^1$ and $R^2$ have the meanings given for the formula I, $Y^3$ represents a chlorine or bromine atom, and Z represents a hydroxy group and either X represents a hydrogen atom and W represents a hydroxy group or X and W together represent an oxygen atom, or Z and X together represent an oxygen atom and W represents a hydroxy group, with a selective metal salt reducing agent, or dehydrating a compound of the general formula II, in which $Y^1$, $Y^2$, $R^1$ and $R^2$ have the meanings given for the general formula I, $Y^3$ and X both represent hydrogen atoms, and W and Z both represent hydroxy groups, using any suitable dehydrating agent.

If in the reduction of a starting compound II, two or three of $Y^1$, $Y^2$ and $Y^3$ represent different halogen atoms, it is the halogen atom of highest molecular weight which is removed during the process. Thus, for example, to prepare a compound of the general formula I, in which both $Y^1$ and $Y^2$ represent bromine atoms, a starting material is used in which $Y^3$ also represents a bromine atom, while to prepare a compound of the general formula I, in which both $Y^1$ and $Y^2$ represent chlorine atoms, a starting material in which $Y^3$ represents either a chlorine or a bromine atom may be used.

The reaction conditions for the reduction process must be such that the acid group in a compound II, where Z represents a hydroxy group, is not reduced, and this depends principally on a suitable choice of selective reducing agent. For example, lithium aluminium hydride cannot be used since it attacks the acid group, but modified alkali metal aluminium hydrides, such as lithium aluminium (tri-t-butoxy)hydride, may be used.

Suitable reducing agents include those of the following formulae:

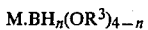

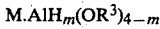

in which M represents an alkali metal, $R^3$ represents an alkyl group having 1 to 4 carbon atoms, n represents an integer 1 to 4, and m represents an integer 1 to 3. Typical reduction agents of this type include lithium borohydride, sodium borohydride, aluminium tri-isopropoxide, (generally used in the presence of isopropyl alcohol), lithium aluminium (tri-t-butoxy)hydride and sodium dithionite. Sodium borohydride is especially preferred.

The reaction medium chosen for the reduction depends, of course, on the reducing agent chosen since certain reducing agents will react with protic solvents. In general, a suitable solvent may be selected from water, dimethylsulfoxide, sulfolane, N-methylpyrrolidone, acetonitrile, alcohols, for example, isopropanol, amides, for example, dimethylformamide or dimethylacetamide, and ethers, for example, tetrahydrofuran. Mixtures of solvents may often be useful.

The reduction is preferably conducted at elevated temperature, especially when $Y^3$ represents a chlorine atom. Preferably, the reaction temperature is at least 50° C., for example, in the range from about 50° C. to about 150° C., especially about 60° C. to about 120° C.

Choice of reaction conditions may have a marked effect on the yield of the compound of the general formula I. For instance, if sodium borohydride is used as reducing agent and water as solvent, and the reaction is carried out at room temperature, the yield of the compound of the general formula I tends to be low if $Y^3$ represents a chlorine atom, but rather higher if $Y^3$ represents a bromine atom. If, however, an aprotic solvent such as dimethylformamide is used and the reaction is conducted at an elevated temperature, the yield of the compound of the general formula I is increased.

In the preparation of a compound of the formula I from a compound of the formula IIa

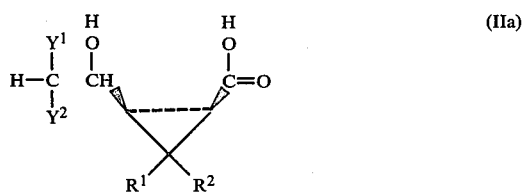

(IIa)

(wherein in formula II $Y^3$ and X both represent hydrogen atoms and W and Z both represent hydroxy groups), suitable dehydrating agents include acids, for example, mineral acids such as sulphuric or phosphoric acid, or organic acids, for example, p-toluene sulphonic acid or acetic acid; acid anhydrides, for example, acetic anhydride or phosphoric anhydride; and acid chlorides, for example, phosphorus trichloride, phosphorus oxychloride or acetyl chloride. Phosphorus trichloride and p-toluene sulphonic acid are preferred dehydrating agents.

The dehydrating process is suitably carried out in the presence of an inert solvent, for example, a hydrocarbon or halogenated hydrocarbon, such as benzene, toluene, chloromethane or trichloromethane, an ether, for example, tetrahydrofuran or diethyl ether, N-methylpyrrolidone, acetonitrile or dimethylsulphoxide. The reaction temperature may vary widely depending on the dehydrating agent used, but is preferably in the range of from about 15° C. to about 150° C. Room temperature is often convenient, for example, when using phosphorus trichloride. When using an acid as dehydrating agent, it is often convenient to carry out the reaction at the reflux temperature of the solvent used, while azeotropically distilling off water.

A compound of formula II which contains a $CY^1Y^2Y^3.CO-$ group and a $-CO_2H$ group cis to each other, is the keto tautomer of a lactol of formula II in which Z and X together represent an oxygen atom. In solution, these keto-lactol tautomers generally co-exist as an equilibrium mixture. Local conditions of temperature, solvent, etc., determine the relative proportions of the tautomers in the equilibrium mixture. These tautomers of formula II can be prepared by the reaction of an anhydride of the general formula III

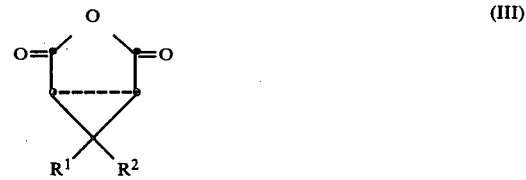

(III)

with a trihalo compound of the general formula IV

(IV)

in which $Y^1$, $Y^2$, $Y^3$, $R^1$ and $R^2$ have the meanings given above, and M represents an alkali metal, for example, sodium or potassium. The reaction is preferably carried out in an inert polar aprotic solvent, for example, acetonitrile. The reaction temperature may, for example, be in the range of from about $-60°$ C. to about 60° C.

A compound of formula II in which $Y^3$ represents a chlorine or bromine atom, X represents a hydrogen atom and both of W and Z represent hydroxy groups may be prepared as disclosed in U.S. Pat. No. 4,166,063 by reaction of a compound of the formula V

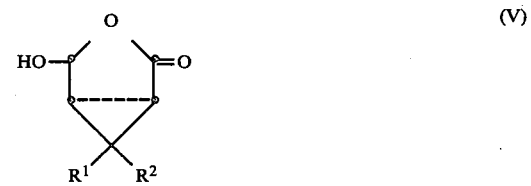

(V)

with a compound of the formula VI

$CH.Y^1Y^2Y^3$ (VI)

in which $R^1$, $R^2$, $Y^1$, $Y^2$ and $Y^3$ have the meanings given above in the presence of a base. Suitable bases include alkali metal alkoxides, hydrides and hydroxides, and the reaction is preferably carried out in the presence of an organic solvent, for example an alkanol, dimethylformamide, dimethylsulphoxide, an ether or an aliphatic hydrocarbon.

A compound of the general formula II in which $Y^3$ represents a hydrogen atom, may be prepared by reduction of a cis keto acid of the general formula VII and/or its lactol tautomer of the general formula VIII:

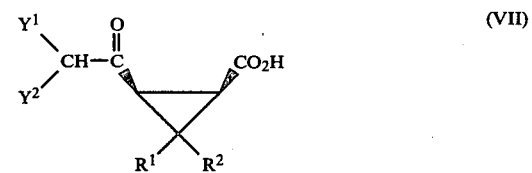

(VII)

-continued

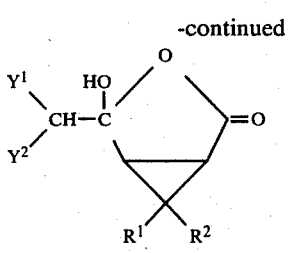
(VIII)

in which $Y^1$, $Y^2$, $R^1$ and $R^2$ have the meanings given above, using any suitable reducing agent. Especially suitable reducing agents are the same preferred metal salts described above, especially alkali metal borohydrides, for example sodium borohydride, and suitable solvents also include those described above.

The compounds of the formulae VII and VIII exhibit the same type of tautomerism as described above. They can be prepared by catalytic hydrogenation of the keto-lactol tautomers of formula II described above in which $Y^3$ represents a chlorine or bromine atom, W and X together represent an oxygen atom and Z represents a hydroxy group, in a suitable solvent. The use of a palladium charcoal catalyst in an alkanoic acid such as propionic acid or, especially, acetic acid as reaction medium is preferred, and the reduction is conveniently carried out at room temperature.

A compound of the general formula I can be converted into a corresponding 2,2-dihalovinyl derivative, and the invention therefore also provides a process for the preparation of a cis dihalovinylcyclopropane carboxylic acid of the general formula IX

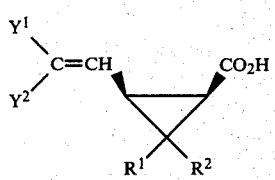
(IX)

in which $Y^1$, $Y^2$, $R^1$ and $R^2$ have the meanings given for the general formula I, which comprises reacting a compound of the general formula I with a base.

The base is suitably a strong base and may for example be an alkali metal hydroxide, hydride or alkoxide, for example sodium hydroxide or potassium tertiary butoxide. Alkali metal alkoxides are especially preferred. Any suitable solvent, for example dimethylsulphoxide, N-methylpyrrolidone, an alcohol, such as methanol, an ether, such as tetrahydrofuran, or an amide, such as dimethylacetamide, may be used. It may be convenient to use a solvent for the compound of the general formula I in which the base is insoluble, for example dioxan, and to conduct the reaction using solid base in the presence of a phase-transfer catalyst, for example tetrabutylammonium chloride. The reaction is suitably carried out at a temperature in the range of from about 0° C. to about 100° C. It may be convenient to carry out the reaction at room temperature or at the reflux temperature of the solvent used.

By a suitable choice of reaction conditions, it may be convenient to prepare a compound of the general formula I and then, without intermediate isolation or workup, to convert it in situ into a compound of the general formula IX.

If an optically active compound of the general formula I is prepared, for example one having the R configuration at the cyclopropane carbon atom bearing the $—CO_2—$ group, reaction with a base normally proceeds with retention of configuration to give the corresponding optical isomer of the compound of the general formula IX. Optically active compounds of the general formula I may be prepared by standard methods, for example by starting from optically active starting materials or by separating the racemic mixture.

EXAMPLES

The following Examples illustrate the invention. All NMR data are given in units of ppm using tetramethyl silane as standard.

EXAMPLE 1

Preparation of cis 2-trichloroacetyl-3,3-dimethylcyclopropane carboxylic acid and its lactol tautomer A suspension of sodium trichloroacetate (0.74 g. 4.0 mmol) in 10 ml acetonitrile and caronic anhydride (0.5 g) was stirred for 20 hours at room temperature. The reaction mixture was then acidified with 0.5 ml concentrated HCl, diluted with water and extracted with dichloromethane. The extracts were washed with water, dried over magnesium sulphate, filtered and evaporated to dryness. 0.8 g of a white solid were obtained. A solution of this solid in $CDCl_3$ was shown by NMR to contain a mixture of cis 2-trichloroacetyl-3,3-dimethylcyclopropane carboxylic acid and its lactol tautomer, 4-hydroxy-4-trichloromethyl-6,6-dimethyl-3-oxabicyclo[3.1.0]hexan-2-one.

EXAMPLE 2

Preparation of cis 2-dichloroacetyl-3,3-dimethylcyclopropane carboxylic acid and its lactol tautomer A crude mixture containing 84% of the tautomers described in Example 1 and 16% caronic anhydride (4.0 g. prepared by the method of Example 1) was added to 20 ml acetic acid and 100 mg of 10% palladium on charcoal. Hydrogen was bubbled through the stirred mixture for 4¼ hours at room temperature. The mixture was then filtered, the solvent was removed under reduced pressure, 20 ml toluene was added to the residue, and the mixture was filtered. The filtrate was evaporated under reduced pressure leaving 2.8 g of an oil. NMR showed that an 80% yield of cis 2-dichloroacetyl-3,3-dimethylcyclopropane carboxylic acid and its lactol tautomer, 4-hydroxy-4-dichloromethyl-6,6-dimethyl-3-oxabicyclo[3.1.0]hexan-2one, had been obtained.

| $^{13}C$ NMR results | | |
|---|---|---|
| keto Acid | endo lactol | exo lactol |
| 14.9 | 17.2 | 16.8 |
| 27.4 | 25.8 | 27.9 |
| 31.2 | 26.4 | 28.3 |
| 33.6 | 31.7 | 32.2 |
| 35.0 | 34.0 | 36.2 |
| 70.0 | 74.8 | 72.0 |
| 174.4 | 104.6 | 102.9 |
| 192.6 | 172.6 | 174.9 |

EXAMPLE 3

Preparation of cis 2-(1-hydroxy-2,2-dichloroethyl)-3,3-dimethylcyclopropane carboxylic acid A portion of the crude reaction mixture of Example 2 (9 mmol product) was dissolved in a solution of sodium bicarbonate (10 mmol) in water (10 ml) at room temperature, and sodium borohydride (4.5 mmol) was added. After stirring for 1½ hours at room temperature, the solution was extracted with chloroform, acidified with concentrated HCl, and extracted again with chloroform. Filtration and evaporation left 1.5 g of an oil which was shown by NMR to contain 90% of the desired product, as a mixture of two diasterioisomers in a ratio approximately 15:1.

| $^{13}$C NMR | |
|---|---|
| isomer 1 | isomer 2 |
| 14.59 | 15.56 |
| 26.68 | 28.12 |
| 28.65 | 28.24 |
| 29.53 | 28.77 |
| 34.30 | 35.36 |
| 71.47 | 72.00 |
| 76.47 | 75.47 |
| 176.90 | 177.34 |

EXAMPLE 4

Preparation of 4-dichloromethyl-6,6-dimethyl-3-oxabicyclo[3.1.0]hexan-2-one

Phosphorus trichloride (4.5 mmol) was added to a solution of the crude hydroxy acid prepared as in Example 3 (4.4 mmol) in chloroform (10 ml). After stirring for ½ hour at 40° C. and washing with a saturated sodium bicarbonate solution, the organic phase was dried over magnesium sulphate, filtered and evaporated under reduced pressure, to give 0.45 g of an oil shown by NMR to contain 76% of the desired product, largely in the form of endo isomer but with some exo isomer present (approximate ratio 15:1).

| $^{13}$C NMR | |
|---|---|
| endo isomer | exo isomer |
| 17.48 | 14.97 |
| 24.74 | 23.08 |
| 25.73 | 25.05 |
| 30.78 | 30.37 |
| 32.62 | 30.97 |
| 69.09 | 72.05 |
| 83.09 | 78.73 |
| 171.87 | 172.10 |

EXAMPLE 5

Preparation of 4-dichloromethyl-6,6-dimethyl-3-oxabicyclo[3.1.0]hexan-2-one

Sodium borohydride (0.12 mmol) was added to a solution of cis 2-(1-hydroxy-2,2,2-trichloroethyl)-3,3-dimethycyclopropane carboxylic acid (0.12 mol) in dry dimethylformamide (0.4 ml), and the mixture was heated for 30 minutes at 80° C. An additional amount of 0.12 mmol sodium borohydride was then added and the mixture was heated for a further 15 minutes at 80° C. It was then diluted with water, acidified with concentrated HCl and extracted with deuterochloroform, CDCl$_3$. The extract was washed with water and analysed by NMR, which showed a yield of 25% of the desired product, with 30% of unconverted starting material.

EXAMPLE 6

Preparation of 4-dichloromethyl-6,6-dimethyl-3-oxabicyclo[3.1.0]hexan-2-one

Sodium borohydride (0.36 mmol) and the keto/lactol tautomers described in Example 1 (0.17 mmol) were dissolved in dry dimethylformamide (0.4 ml) and heated for 3 hours at 80° C. The reaction mixture was then diluted with water, acidified with concentrated HCl, and extracted with CDCl$_3$. The extract was washed with water and analysed by NMR, which showed a yield of 28% of the desired compound.

EXAMPLE 7

Preparation of 4-dibromomethyl-6,6-dimethyl-3-oxabicyclo[3.1.0]hexan-2-one

Cis-2-tribromoacetyl-3,3-dimethylcyclopropane carboxylic acid (0.2 mmol) prepared by a method analogous to that described in Example 1, was stirred for 10 minutes with a solution of sodium borohydride (0.8 mmol) in 5 ml water at room temperature for 16 hours and the crystalline reaction product was then filtered off and dried under reduced pressure at 40° C. The resulting product weighed 13 mg and contained 50% of the desired product, largely in the form of the endo isomer.

| Proton NMR in CDCl$_3$ | |
|---|---|
| 1.20 (s, 3H) | |
| 1.37 (s, 3H) | |
| 2.23 (m, 2H) | |
| 5.00 (dd, 1H) coupling constants | J = 5 Hz |
| | J = 10 Hz |
| 5.72 (d, 1H) J = 10 Hz | |

EXAMPLE 8

Preparation of cis 2-(2,2-dichlorovinyl)-3,3-dimethylcyclopropane carboxylic acid Potassium tertiary butoxide (0.45 mmol) was added to a solution of 4-dichloromethyl-6,6-dimethyl-3-oxabicyclo[3.1.0]hexan-2-one (0.16 mmol) in dry dimethylsulphoxide (0.4 ml) and stirred at room temperature for ½ hour. The solution was then diluted with water, acidified with concentrated hydrochloric acid and extracted with CDCl$_3$. NMR analysis showed a virtually quantitative yield of the desired cis acid.

EXAMPLE 9

Preparation of cis 2-(2,2-dichlorovinyl)-3,3-dimethylcyclopropane carboxylic acid A solution of 2.5 mmol sodium hydroxide in 5 ml absolute ethanol was mixed with 4-dichloromethyl-6,6-dimethyl-3-oxabicyclo[3.1.0]hexan-2-one (0.1 mmol) and heated for 2 hours at 55° C. The solvent was then removed under reduced pressure, and the residue was diluted with water, acidified with concentrated hydrochloric acid and extracted with CDCl₃. NMR indicated a yield of 24% of the desired cis acid.

I claim:

1. A process for the preparation of a (cis)-dihalovinyl-cyclopropanecarboxylic acid of the formula:

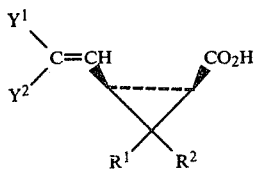

wherein each of $Y^1$ and $Y^2$ independently represents a fluorine, chlorine or bromine atom and each of $R^1$ and $R^2$ independently represents a hydrogen atom or an alkyl group having up to 10 carbon atoms, or $R^1$ and $R^2$ together represent an alkylene group having from 2 to 5 carbon atoms which comprises treating a compound of the formula

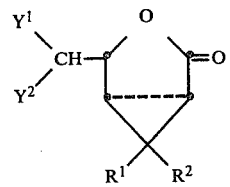

wherein $Y^1$, $Y^2$, $R^1$ and $R^2$ have the above stated meanings, with a base.

2. A process according to claim 1, wherein the base is an alkali metal hydroxide, hydride or alkoxide.

3. A process according to claim 2 wherein the base is an alkali metal hydroxide.

4. A process according to claim 3 wherein the base is sodium hydroxide.

* * * * *